(12) United States Patent
Thommen et al.

(10) Patent No.: US 6,693,218 B1
(45) Date of Patent: Feb. 17, 2004

(54) PROCESS FOR THE PREPARATION OF KETIMINES

(75) Inventors: Marc Thommen, Toffen (SE); Andreas Hafner, Gelterkinden (SE); Roman Kolly, Allschwil (SE); Hans-Jörg Kirner, Pratteln (SE); Frédéric Brunner, Chézard (SE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/130,199

(22) PCT Filed: Nov. 7, 2000

(86) PCT No.: PCT/EP00/10970

§ 371 (c)(1),
(2), (4) Date: Sep. 20, 2002

(87) PCT Pub. No.: WO01/36377

PCT Pub. Date: May 25, 2001

(30) Foreign Application Priority Data

Nov. 16, 1999 (EP) .............................................. 99811055

(51) Int. Cl.⁷ ...................... C07C 249/02; C07C 209/88
(52) U.S. Cl. ...................................... 564/270; 564/308
(58) Field of Search ................................. 564/270, 308

(56) References Cited

U.S. PATENT DOCUMENTS

| | | | |
|---|---|---|---|
| 4,536,518 A | 8/1985 | Welch, Jr. et al. ........... | 514/647 |
| 4,855,500 A | 8/1989 | Spavins ...................... | 564/270 |
| 5,019,655 A | 5/1991 | Adrian ........................ | 568/322 |

FOREIGN PATENT DOCUMENTS

| | | |
|---|---|---|
| WO | 99/36394 | 7/1999 |
| WO | 99/47486 | 9/1999 |
| WO | 00/26181 | 5/2000 |

OTHER PUBLICATIONS

Houben–Weyl Methoden Der Organischen Chemie, vol. E14b, No. 1, pp. 239–242.

*Primary Examiner*—Peter O'Sullivan
(74) *Attorney, Agent, or Firm*—Kevin T. Mansfield

(57) ABSTRACT

Described is a process for the preparation of compounds of formula (1a) which comprises reacting an isomeric mixture consisting of from 75 to 95% of compound of formula (2a) and from 5 to 25% of a compound of formula (2b) with methylamine, in a suitable solvent, to form a sertraline-imine isomeric mixture consisting of from 75 to 95% of formula (1a) and from 5 to 25% of formula (1b)($A_1$), or reacting an isomeric mixture consisting of from 75 to 95% of a compound of formula (2a) and from 5 to 25% of a compound of formula (2b) with methylamine, in a suitable solvent, using suitable methods of isolation to form an enriched sertraline-imine isomeric mixture, consisting of >99% of a compound of formula (1a) and <1% of a compound of formula (1b)($A_2$); and then subjecting the sertraline-imine isomeric mixture obtained according to reaction route ($A_1$) or ($A_2$), in a suitable solvent, to recrystallisation (B), in accordance with scheme (I) wherein in formula (1a), $R_1$, $R_2$ and $R_3$ are each independently of the others hydrogen, halogen, trifluoromethyl or $C_1$–$C_4$alkoxy and formulae (1b), (2a) and (2b) are as defined in the description.

36 Claims, No Drawings

PROCESS FOR THE PREPARATION OF KETIMINES

This application is a 371 of PCT/EP00/10970 filed Nov. 7, 2000.

The present invention relates to a process for the preparation of ketimines, which are suitable as starting materials for the preparation of pharmaceutical active ingredients having antidepressant properties, for example sertraline.

Processes for the preparation of ketimines are described, for example, in U.S. Pat. No. 4,536,518 and U.S. Pat. No. 4,855,500.

The process for the preparation of ketimines disclosed in U.S. Pat. No. 4,536,518 (columns 9/10, Example 1(F)) comprises reaction of the ketone in an aprotic solvent, for example tetrahydrofuran, with methylamine in the presence of titanium tetrachloride, with cooling. A disadvantage of that process is the need to work with tetrahydrofuran, which is readily combustible, and with titanium tetrachloride, which is not innocuous from an ecological standpoint. In addition, the procedure is expensive, because the reaction is carried out with cooling. A further disadvantage of the process concerns the working up. The product has to be precipitated with additional hexane.

The process for the preparation of ketimines disclosed in U.S. Pat. No. 4,855,500 (columns 5/6, claim 1) comprises reaction of the ketone in an aprotic solvent, for example methylene chloride, toluene or tetrahydrofuran, with anhydrous methylamine in the presence of molecular sieve, with cooling.

That process, too, has the disadvantage of the need to work, under anhydrous conditions, with solvents that are not innocuous from an ecological standpoint, such as methylene chloride, or with readily combustible solvents, such as tetrahydrofuran. The molecular sieve used is expensive and has to be recycled in an additional step. A further disadvantage of the process is that the molecular sieve needs to be removed and the product has to be precipitated with additional hexane.

U.S. Pat. No. 5,019,655 describes a one-step process for the preparation of 4-dichlorophenyl-1-tetralones having a degree of purity of from 98 to 99%. It is disclosed that a plurality of recrystallisation operations are required at the ketone stage, using large amounts of solvents, in order to achieve a degree of purity >99.5%.

The need therefore exists for the discovery of an efficient process for the preparation of ketimines that does not have the above-listed disadvantages, especially in relation to the solvents and recrystallisation steps used.

Surprisingly, it has now been found that the desired degree of purity of ketimines can be achieved by carrying out the recrystallisation at the imine stage and using sertralone, precipitated in crude form, in the imine synthesis. At the same time high yields are achieved, and substantially smaller amounts of solvents are sufficient for the recrystallisation.

The present invention accordingly relates to a process for the preparation of compounds of formula (1a)

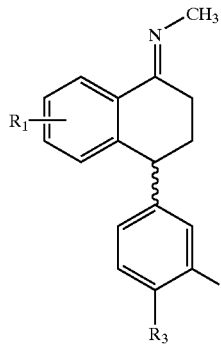

$R_2$, which comprises reacting (a) an isomeric mixture consisting of from 75 to 95% of a compound of formula (2a)

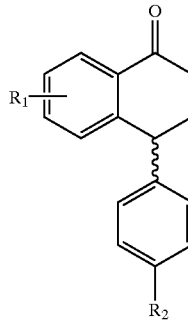

and from 5 to 25% of a compound of fromula (2b)

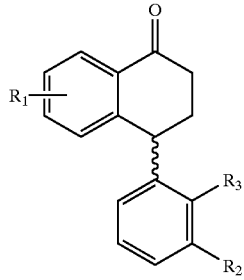

with methylamine, in a suitable solvent, to form sertraline-imine isomeric mixture consisting of from 75 to 95% of formula (1a) and from 5 to 25% o formula (1b)

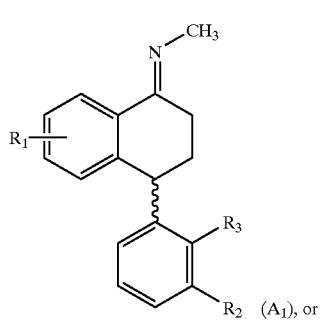

($A_1$), or reacting an isomeric mixture consisting of from 75 to 95% of a compound of formula (2a) and from 5 to 25% of a compound of formula (2b) with methylamine, in a suitable solvent, using suitable methods of isolation to form an enriched sertraline-imine isomeric mixture, consisting of >99% of a compound of formula (1a) and <1% of a compound of formula (1b) ($A_2$);

and then subjecting the sertraline-imine isomeric mixture obtained according to reaction route ($A_1$) or ($A_2$), in a suitable solvent, to recrystallisation (B), in accordance with the following scheme:

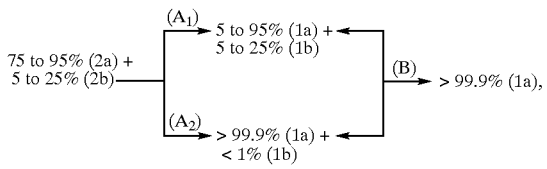

wherein in formulae (1a), (1b), (2a) and (2b)

$R_1$, $R_2$ and $R_3$ are each independently of the others hydrogen, halogen, trifluoromethyl or $C_1$–$C_4$alkoxy.

The solvents preferably used for reaction routes ($A_1$), ($A_2$) and (B) are selected from (a) $C_1$–$C_{24}$amines,
(b) $C_1$–$C_{12}$nitriles,
(c) $C_2$–$C_{24}$carboxylic acid esters,
(d) $C_3$–$C_{24}$ortho esters,
(e) $C_2$–$C_{24}$ethers,
(f) $C_1$–$C_{24}$alkanes,
(g) aromatic solvents,
(h) amides,
(i) sulfoxides,
(k) halogenated solvents,
(l) supercritical $CO_2$, and
(m) protic solvents.

Especially preferred solvents (a) are selected from aliphatic monoamines, especially methylamine, nitrogen heterocycles, and aliphatic and aromatic, non-substituted or substituted secondary and tertiary mono-, di- and tri-amines.

Further preferred solvents (a) correspond to formula (3)

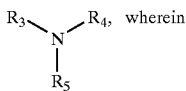

$R_3$ is hydrogen; $C_1$–$C_5$alkyl; hydroxy-$C_1$–$C_5$alkyl; $C_5$–$C_7$cycloalkyl; non-substituted phenyl or phenyl substituted by one or more $C_1$–$C_5$alkyl groups, by halogen or by nitro; non-substituted phenyl-$C_1$–$C_3$alkyl or phenyl-$C_1$–$C_3$alkyl substituted by one or more $C_1$–$C_5$alkyl groups, by halogen or by nitro;

$R_4$ and $R_5$ are each independently of the other $C_1$–$C_5$alkyl; $C_5$–$C_7$cycloalkyl; hydroxy-$C_1$–$C_5$alkyl; non-substituted phenyl or phenyl substituted by one or more $C_1$–$C_5$alkyl groups, by halogen or by nitro; non-substituted phenyl-$C_1$–$C_3$alkyl or phenyl-$C_1$–$C_3$alkyl substituted by one or more $C_1$–$C_5$alkyl groups, by halogen or by nitro; or $R_4$ and $R_5$ together with the nitrogen atom form a 3- to 6-membered heterocyclic radical.

There are furthermore preferably used solvents (a) that correspond to formula (4)

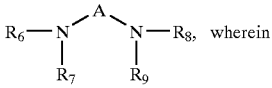

$R_6$ and $R_8$ are each independently of the other hydrogen; $C_1$–$C_5$alkyl; or $C_5$–$C_7$cycloalkyl, $R_7$ and $R_9$ are each independently of the other $C_1$–$C_5$alkyl; $C_5$–$C_7$cycloalkyl; non-substituted phenyl or phenyl substituted by one or more $C_1$–$C_5$alkyl groups, by halogen or by nitro; non-substituted phenyl-$C_1$–$C_3$alkyl or phenyl-$C_1$–$C_3$alkyl substituted by one or more $C_1$–$C_5$alkyl groups, by halogen or by nitro, or $R_6$ and $R_7$, $R_8$ and $R_9$, or $R_7$ and $R_9$, as the case may be, form a 3- to 6-membered heterocyclic radical; and $A_2$ is $C_1$–$C_5$alkylene.

The following may be mentioned as representative examples of solvents (a) for use in accordance with the invention:

as aliphatic monoamines, e.g. methylamine, dimethylamine, triethylamine, diethylamine, triethylamine, di-n-propylamine and tri-n-propylamine;

as nitrogen heterocycles, ethylene-imine, pyrrolidine, piperidine and morpholine, as aliphatic diamines, e.g. N,N-dimethylethylenediamine and hexamethylenediamine;

as aromatic monoamines, e.g. N-methylaniline and N,N-dimethylaniline;

as substituted aromatic monoamines, e.g. o-, m- and p-toluidine, 2-, 3- and 4-chloroaniline, 2-, 3- and 4-nitroaniline;

as aromatic diamines, e.g. o-, m- and p-phenylenediamine.

Preferably used solvents (b) correspond to formula

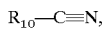 (5) wherein $R_{10}$ is straight-chain or branched $C_1$–$C_{12}$alkyl; $C_5$–$C_7$cycloalkyl; non-substituted phenyl or phenyl substituted by one or more $C_1$–$C_5$alkyl groups, by halogen or by nitro; non-substituted phenyl-$C_1$–$C_3$alkyl or phenyl-$C_1$–$C_3$alkyl substituted by one or more $C_1$–$C_5$alkyl groups, by halogen or by nitro.

Representative examples of that group of solvents include acetonitrile and benzonitrile.

As solvents (c) there are preferably used compounds of formula (6)

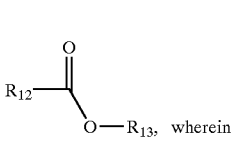

$R_{12}$ and $R_{13}$ are each independently of the other straight-chain or branched $C_1$–$C_{12}$alkyl; $C_5$–$C_7$cycloalkyl; non-substituted phenyl or phenyl substituted by one or more $C_1$–$C_5$alkyl groups, by halogen or by nitro; non-substituted phenyl-$C_1$–$C_3$alkyl or phenyl-$C_1$–$C_3$alkyl substituted by one or more $C_1$–$C_5$alkyl groups, by halogen or by nitro.

Representative examples of such solvents include acetates, e.g. methyl acetate and ethyl acetate.

Solvents (d) preferably used according to the invention correspond to formula (7)

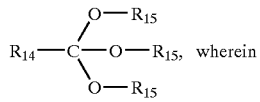

$R_{14}$ is hydrogen; straight-chain or branched $C_1$–$C_5$alkyl; or $C_5$–$C_7$cycloalkyl; and $R_{15}$ is $C_1$–$C_5$alkyl.

Representative examples of such solvents include orthoformic acid $C_1$–$C_3$alkyl esters, especially orthoformic acid methyl or ethyl ester, and orthoacetic acid $C_1$–$C_3$alkyl esters, especially orthoacetic acid ethyl ester.

Solvents (e) preferably used according to the invention correspond to formula $$R_{16}\text{—}O\text{—}R_{17}, \qquad (8)$$

wherein $R_{16}$ and $R_{17}$ are each independently of the other straight-chain or branched $C_1$–$C_{12}$alkyl; or $C_5$–$C_7$cycloalkyl.

Representative examples of such solvents include dimethyl ether, diethyl ether, methyl ethyl ether, methyl n-propyl ether, methyl isopropyl ether, diisopropyl ether, dibutyl ether and tert-butyl methyl ether. Polyethers can also be used.

Solvents (f) preferably used according to the invention are saturated $C_6$–$C_{22}$hydrocarbons, e.g. hexane, neohexane, heptane, octane, isooctane, nonane, decane, undecane, dodecane, tridecane, tetradecane, pentadecane, hexadecane, heptadecane, octadecane, nonadecane, eicosane, heneicosane and docosane.

Solvents (g) preferably used according to the invention are benzene, toluene, xylene and xylene isomeric mixtures.

Solvents (h) preferably used according to the invention are especially aliphatic and aromatic amides corresponding to formula (9)

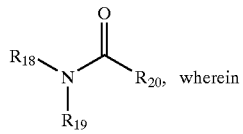

$R_{18}$ and $R_{19}$ are each independently of the other hydrogen; $C_1$–$C_5$alkyl; or $C_5$–$C_7$cycloalkyl, and $R_{20}$ is $C_1$–$C_5$alkyl; $C_5$–$C_7$cycloalkyl; non-substituted phenyl or phenyl substituted by one or more $C_1$–$C_5$alkyl groups, by halogen or by nitro; or non-substituted phenyl-$C_1$–$C_3$alkyl or phenyl-$C_1$–$C_3$alkyl substituted by one or more $C_1$–$C_5$alkyl groups, by halogen or by nitro.

Examples of solvents (i) correspond to formula $$R_{21}\text{—}(S\text{=}O)\text{—}R_{22}, \qquad (10)$$

wherein $R_{21}$ and $R_{22}$ are each independently of the other $C_1$–$C_5$alkyl; $C_5$–$C_7$cycloalkyl; non-substituted phenyl or phenyl substituted by one or more $C_1$–$C_5$alkyl groups, by halogen or by nitro; or non-substituted phenyl-$C_1$–$C_3$alkyl or phenyl-$C_1$–$C_3$alkyl substituted by one or more $C_1$–$C_5$alkyl groups, by halogen or by nitro.

Examples of solvent (k) correspond to formula $$ClCR_{23}R_{24}R_{25}, \qquad (11a)$$

$$Cl_2CR_{26}R_{27} \qquad (11b) \text{ or}$$

$$Cl_3CR_{28}, \qquad (11c)$$

wherein $R_{23}$, $R_{24}$, $R_{25}$, $R_{26}$, $R_{27}$ and $R_{28}$ are each independently of the others $C_1$–$C_5$alkyl; $C_5$–$C_7$cycloalkyl; non-substituted phenyl or phenyl substituted by one or more $C_1$–$C_5$alkyl groups, by halogen or by nitro; or non-substituted phenyl-$C_1$–$C_3$alkyl or phenyl-$C_1$–$C_3$alkyl substituted by one or more $C_1$–$C_5$alkyl groups, by halogen or by nitro.

Representative examples of that class of solvents include dichloroethane, dichloropropane, trichloroethane; and also haloaromatic compounds, e.g. chlorobenzene and dichlorobenzene.

When supercritical $CO_2$ is used, the reaction is carried out at a temperature $T \geq T_{crit}$ and $p \geq p_{crit}$ in $CO_2$ as solvent. Following the reaction, $CO_2$ is evaporated off and the imine is discharged in the form of a solid.

The protic solvent (m) is preferably an alcohol that corresponds especially to formula $$X(OH)_b \qquad (12)$$

wherein b is 1, 2, 3 or 4, and, when b is 1,

X is $C_1$–$C_8$alkyl, $C_5$–$C_8$cycloalkyl or —$CH_2CH_2(OCH_2CH_2)_cR_{21}$, c is 0, 1 or 2, and $R_{21}$ is $C_1$–$C_4$alkoxy, or, when b is 2, X is $C_2$–$C_8$alkylene or —$CH_2CH_2(OCH_2CH_2)_c$—, c having the meanings given above, or, when b is 3, X is $C_3$–$C_8$alkanetriyl or $N(CH_2CH_2)_3$, or, when b is 4, X is $C_4$–$C_8$alkanetetrayl.

A preferred meaning of X (when b=1) is, for example, $C_1$–$C_6$alkyl, especially $C_1$–$C_4$alkyl, e.g. ethyl or isopropyl.

A preferred meaning of X (when b=2) is, for example, $C_2$–$C_6$alkylene, especially $C_2$–$C_4$alkylene, e.g. ethylene.

Of particular interest is a process for the preparation of compounds of formula (1) in which the protic solvent is a compound of formula (12) wherein b is 1 or 2, and, when b is 1, X is $C_1$–$C_4$alkyl or $C_5$–$C_6$cydoalkyl, or, when b is 2, X is $C_2$–$C_4$alkylene.

Alcohols that are relevant in practice are methanol, ethanol, isopropanol, n-butanol, ethylene glycol, methyl Cellosolve, ethyl Cellosolve, cyclohexanol, glycerol, diethylene glycol, triethanolamine, polyethylene glycol, sec-butanol, n-propanol and tert-butanol.

In the above definitions of the radicals $R_1$ to $R_{21}$:

$C_1$–$C_{12}$alkyl is a branched or unbranched hydrocarbon radical, for example methyl, ethyl, n-propyl, isopropyl, n-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3- tetramethylbutyl, 1-methylheptyl, 3-methylheptyl, n-octyl, 2-ethylhexyl, isooctyl, nonyl, decyl, undecyl or dodecyl;

$C_5$–$C_8$cycloalkyl is, for example, cyclopentyl, cycloheptyl, cyclooctyl or, preferably, cyclohexyl;

$C_1$–$C_4$alkoxy is a branched or unbranched hydrocarbon radical, for example methoxy, ethoxy, propoxy, isopropoxy, n-butoxy, isobutoxy or tert-butoxy. Preference is given to methoxy;

$C_2$–$C_{18}$alkenyl is, for example, allyl, methallyl, isopropenyl, 2-butenyl, 3-butenyl, isobutenyl, n-penta-2,4-dienyl, 3-methylbut-2-enyl, n-oct-2-enyl, nodec-2-enyl, isododecenyl, n-dodec-2-enyl or n-octadec-4-enyl;

$C_3$–$C_{12}$alkynyl is $C_3$–$C_{12}$alkenyl that is doubly unsaturated one or more times, wherein the triple bonds may optionally be isolated or conjugated with one another or with double bonds, e.g. 1-propyn-3-yl, 1-butyn-4-yl, 1-pentyn-5yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl or 1-decyn-10-yl;

$C_2$–$C_8$alkylene is a branched or unbranched radical, for example ethylene, propylene, trimethylene, tetramethylene, pentamethylene, hexamethylene, heptamethylene or octamethylene.

Alkanetriyl having from 3 to 8 carbon atoms is derived from an alkane having from 3 to 8 carbon atoms, has 3 hydrogen atoms missing and is, for example

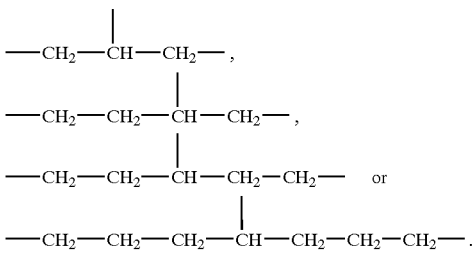

Glyceryl is preferred.

$C_4$–$C_8$Alkanetetrayl is derived from an alkane having from 4 to 8 carbon atoms, has 3 hydrogen atoms missing and is

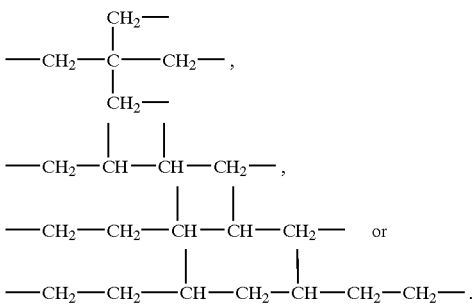

Pentaerythrityl is preferred.

Halogen is, for example, chlorine, bromine or iodine. Chlorine is preferred.

It is furthermore possible for further solubilising or solubility-inhibiting additives (e.g. toluene, cyclohexane) to be added.

The present process may optionally be carried out in the presence of a catalyst. Preferred catalysts for the process for the preparation of compounds of formula (1) are protonic acids, Lewis acids, aluminium silicates, ion exchange resins, zeolites, naturally occurring layer silicates and modified layer silicates.

Protonic acids are preferred.

Suitable protonic acids include, for example, acids of inorganic or organic salts, e.g. hydrochloric acid; sulfuric acid; phosphoric acid or sulfonic acids, for example methanesulfonic acid, p-toluenesulfonic acid or camphor-10-sulfonic acid.

A suitable Lewis acid is, for example, scandium tristriflate [Sc(OTf)$_3$].

Suitable aluminium silicates include, for example, those widely used in the petrochemical industry and referred to also as amorphous aluminium silicates. Such compounds contain approximately from 10 to 30% silicon dioxide and from 70 to 90% aluminium oxide.

Suitable ion exchange resins include, for example, styrene-divinylbenzene resins that in addition carry sulfonic acid groups, e.g. Amberlite 200® and Amberlyst® from Rohm and Haas and Dowex 50® from Dow Chemicals; perfluorinated ion exchange resins, e.g. NafionH® from DuPont; and other superacidic ion exchange resins as described by T. Yamaguchi, Applied Catalysis, 61, 1–25 (1990) or M. Hino et al., J. Chem. Soc. Chem. Commun. 1980, 851–852.

Suitable zeolites include, for example, those that are widely used in the petrochemical industry as cracking catalysts and that are known in the form of crystalline silicon-aluminium oxides having various crystal structures. Special preference is given to the faujasites from Union Carbide, e.g. Zeolite X®, Zeolite Y® and Ultrastable Zeolite Y®, Zeolite Beta® and Zeolite ZSM-12® from Mobil Oil Co. and Zeolite Mordenit® from Norton.

Suitable naturally occurring layer silicates are also called "acid earths" and include, for example, bentonites and montmorillonites which, on an industrial scale, are broken down, ground, treated with mineral acids and calcined. Especially suitable naturally occurring layer silicates are the Fulcat® types from Laporte Adsorbents Co., e.g. Fulcat 22A®, Fulcat 22B®, Fulcat 20®, Fulcat 30® and Fulcat 40®; and the Fulmont® types from Laporte Adsorbents Co., e.g. Fulmont XMP-3® and Fulmont XMP-4®. An especially preferred catalyst for the process according to the invention is Fulcat 22B®. The other Fulcat® types and Fulmont® types are likewise to be classified in that preferred group, however, because only slight differences exist between the individual types, such as, for example, the number of acid centres.

Modified layer silicates are also called "pillared clays" and are derived from the above-described naturally occurring layer silicates, comprising in addition, between the silicate layers, oxides of, for example, zirconium, iron, zinc, nickel, chromium, cobalt or magnesium. That type of catalyst is widely mentioned in the literature, e.g. as described by J. Clark et al., J. Chem. Soc. Chem. Com. 1989, 1353–1354, but is manufactured by only very few companies. Especially preferred modified layer silicates include, for example, Envirocat EPZ-10®, Envirocat EPZG® and Envirocat EPIC® from Contract Chemicals.

Special preference is given to a process for the preparation of compounds of formula (1a) wherein the catalyst is a sulfonic acid, especially p-toluenesulfonic acid, methanesulfonic acid or camphor-10-sulfonic acid.

The molar ratio of the amount of catalyst used to the amount of methylamine used is advantageously from 0.001:1 to 1:1, especially from 0.01:1 to 0.5:1, e.g. from 0.05:1 to 0.1:1.

A molar ratio of the amount of catalyst to the amount of methylamine of 1:1 means that the methylamine can be used in the process according to the invention also in the form of a salt, e.g. methylamine hydrochloride.

The reaction steps ($A_1$) and ($A_2$) are preferably carried out at a temperature of from 20 to 150° C., especially from 30 to 100° C., where appropriate under slight pressure.

The proportion of starting compounds in the reaction mixture is in the range from 5 to 70% by weight, preferably from 30 to 60% by weight.

Especially preferably, the reaction is carried out using a large molar excess of methylamine.

Special preference is therefore given to a process for the preparation of compounds of formula (1a) wherein the molar ratio of the amount of compound of formula (2a and 2b) to the amount of methylamine is from 1:1 to 1:1000, especially from 1:1.05 to 1:50, e.g. from 1:1.5 to 1:15.

The methylamine can be used in the form of methylamine gas or in the form of a solution in an appropriate solvent.

Of special interest is a process variant in which the reaction can be carried out in pure methylamine under pressure, that compound being used simultaneously as solvent and reagent.

Also of special interest is a process for the preparation of compounds of formula (1a) wherein the compound is continuously crystallised out of the reaction medium to a varying extent during the preparation process and subsequently filtered off.

Also of special interest is a process for the preparation of compounds of formula (1a) wherein the filtrate is used in a further reaction for the preparation of compounds of formula (1a). In that procedure the consumed amounts of the compound of formula (2a) and of methylamine are replenished. Preference is given to from 2 to 10 filtrate-recycling operations.

The process according to the invention is accordingly suitable as a continuous process for the preparation of compounds of formula (1a).

The water formed during the process can optionally be bound to an additional water binder, for example a molecular sieve or ortho ester, e.g. orthoformic acid trimethyl ester.

For isolation of non-enriched sertraline-imine isomeric mixtures (reaction route $A_1$), when the reaction is complete the solvent is distilled off, or methylamine or other gaseous amines are released, and the residue obtained is dried.

For isolation of enriched sertraline-imine isomeric mixtures ($A_2$), the reaction mass is cooled, the suspension is filtered, and the filter cake is washed with the solvent. The product is then dried.

The solvents used for recrystallisation (B) are selected from
(a) $C_1$–$C_{24}$amines,
(b) $C_1$–$C_{12}$nitriles,
(c) $C_2$–$C_{24}$carboxylic acid esters,
(d) $C_3$–$C_{24}$ortho esters,
(e) $C_2$–$C_{24}$ethers,
(f) $C_1$–$C_{24}$alkanes, especially $C_6$–$C_{24}$alkanes,
(g) aromatic solvents,
(h) amides,
(i) sulfoxides,
(k) halogenated solvents,
(l) supercritical $CO_2$,
(m) protic solvents, and
(n) $C_2$–$C_{24}$ketones.

$C_2$–$C_{24}$Ketones (=component (n)) correspond especially to formula (11)

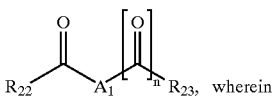, wherein $R_{22}$ and $R_{23}$ are each independently of the other branched or unbranched $C_1$–$C_{12}$alkyl; $C_5$–$C_7$cycloalkyl; $C_2$–$C_{12}$alkenyl; $C_3$–$C_{12}$alkynyl; non-substituted phenyl or phenyl-$C_1$–$C_3$alkyl, or phenyl or phenyl-$C_1$–$C_3$alkyl substituted by one or more $C_1$–$C_5$alkyl groups;

$A_1$ is a direct bond; or $C_1$–$C_5$alkylene; and n is 0; or 1.

Representative examples of that group of ketones include, e.g., aliphatically saturated ketones, e.g. propanone (acetone), butanone (methyl ethyl ketone) and 2-pentanone (methyl propyl ketone); cycloaliphatically saturated ketones, e.g. cyclopentanone, cyclohexanone and cycloheptanone (suberone); aliphatically unsaturated ketones, e.g. 3-buten-2-one, 1,4-pentadien-3-one, 3-pentyn-2-one; aromatic ketones, e.g. benzophenone; aromatic-aliphatic ketones, e.g. methyl phenyl ketone (acetophenone) and propiophenone; diketones, e.g. 2,3-butanedione, 2,4-pentanedione and 2,5-hexanedione; and aromatic diketones, e.g. diphenylethanedione (benzil). In an especially preferred embodiment, recrystallisation (B) is carried out from the same solvent as reaction ($A_1$) or ($A_2$).

The solvents employed in accordance with the invention may be used in the form of individual compounds or in the form of mixtures of two or more individual compounds from the same or different solvent groups (a)–(n).

Recrystallisation (B) is preferably carried out by recrystallising the sertraline-imine isomeric mixture or the enriched sertraline-imine isomeric mixture under reflux. For that purpose the sertraline-imine obtained according to ($A_1$) or ($A_2$), in a suitable solvent, is introduced into a suitable reaction vessel fitted with a stirrer and a reflux condenser. The reaction mass is heated at reflux temperature in an inert gas atmosphere, with stirring, until a clear solution is obtained. The solution is cooled to the appropriate isolation temperature, the product slowly precipitating. The suspension is filtered, and the filter cake is washed with the solvent and dried. Isomerically pure (>99.9%) sertraline-imine of formula (1a) is obtained in a yield of from 80 to 90%, having a sertralone content of from 0.1 to 0.3% (HPLC), a catalyst contamination of $\leq 0.001\%$ and a water content of from 0.1 to 0.3%.

In a further process variant, recrystallisation (B) of the sertraline-imine isomeric mixture or of the enriched sertraline-imine isomeric mixture is carried out under pressure. For that purpose the sertraline-imine obtained by ($A_1$) or ($A_2$) and the solvent are introduced into a suitable pressurized reactor fitted with a stirrer. The reactor is sealed under a nitrogen atmosphere. The stirrer is started and the reaction mixture is heated at the desired reaction temperature until a clear solution is obtained. The solution is cooled to the appropriate isolation temperature, the product slowly precipitating. The suspension is filtered, and the filter cake is washed with the solvent and dried.

The dissolution temperatures in the solvents selected are in the range from 30 to 150° C., preferably from 50 to 150° C. and most preferably from 70 to 120° C.

According to the boiling points of the solvents listed, recrystallisation (B) can be carried out at normal pressure under reflux, or at elevated pressure, generally in the range from 0 to 10 bar, preferably from 0 to 3 bar.

The cooling gradients are in the range from 0.005 to 10° C./min., preferably from 0.05 to 10° C./min and most preferably from 0.1 to 1° C./min.

The isolation temperatures are in the range from −20 to 40° C., preferably from 0 to 25° C.

The concentrations of sertraline-imine in the clear solution are in the range from 5 to 40% by weight, preferably from 15 to 20% by weight.

Adsorbents such as activated charcoal or adsorber resins may be added during the procedure for the purpose of removing impurities that impart colour. Such substances are added in amounts of from 1 to 10% of the clear solution and are removed, while hot, by filtration prior to the crystallisation procedure.

By means of the recrystallisation, it is possible both to improve the product purity and to remove impurities that interfere with the further reaction, such as water or catalyst residues.

The present invention relates also to a process for the preparation of optically pure (cis)- and/or (trans)-sertraline or enantiomerically enriched mixtures of (cis)- and (trans)-sertraline. The process comprises the following reaction steps (I) to (III):

(I) reaction of an isomeric mixture, consisting of from 75 to 95% of formula (2a) and from 25 to 5% respectively of formula (2b), to form the sertraline-imine of formula (1a), corresponding to the process according to claim 1, (II) subsequent cis-selective hydrogenation using noble metal catalysts or other catalysts based on copper or nickel, to form cis-sertraline-enriched mixtures of racemic cis- and trans-sertraline, (III) subsequent racemate cleavage based on mandelic acid for the selective preparation of the desired enantiomerically pure cis-isomer.

Starting from crude sertraline-ketone (isomeric mixture of the compounds of formulae (2a) and (2b)), sertraline-imine is prepared in accordance with the process described in claim 1. The imine is converted to cis-sertraline-enriched mixtures of racemic cis- and trans-sertraline in a subsequent cis-selective hydrogenation using noble metal catalysts or other catalysts based on copper or nickel with a wide variety of supports, e.g. carbon, Alox, aluminium oxide, silica, calcium carbonate, barium carbonate, barium sulfate etc.

The desired enantiomerically pure cis-isomer can be selectively crystallised in a subsequent racemate cleavage based on mandelic acid.

The optically pure amine is freed using sodium hydroxide solution and, as a hydrochloride, is converted in suitable solvents into the desired polymorphous form.

The following Examples illustrate the invention further. Parts or percentages relate to weight.

EXAMPLE 1

Preparation of Sertraline-imine Isomeric Mixture in Ethanol 240 g of sertralone isomeric mixture (95% 3,4-dichlorosertralone, 5% 2,3-dichlorosertralone) and 800 ml of ethanol are introduced into a suitable reaction vessel fitted with a stirrer and a gas inlet. The stirrer is started, the suspension is cooled to 0° C. and 55 g of methylamine are introduced under the level of, that is to say below the surface of, the solvent. After the addition of 10 ml of methanesulfonic acid (catalyst), the reaction mass is heated up and stirred for 3 hours at 50° C. and for 1 hour at 70° C. At 40° C. the reaction mass is concentrated to dryness by evaporation under reduced pressure and the product is isolated.

Yield: 248 g of sertraline-imine in crude dry form having the following composition:

87.8% 3,4-dichlorosertraline-imine 4.6% 2,3-dichlorosertraline-imine 4.9% sertralone 2.7% methanesulfonic acid derivatives and salts.

The original ratio of isomers remains unaltered. The yield of the imine is 95%.

Where a catalyst is used, it can be removed according to customary methods, such as ion exchange, adsorption or recrystallisation from solvents that do not have a tendency towards isomer enrichment.

EXAMPLE 2

Preparation of Sertraline-imine Isomeric Mixture With Isomer Enrichment in Ethanol 240 g of sertralone isomeric mixture (95% 3,4-dichlorosertralone, 5% 2,3-dichlorosertralone) and 800 ml of ethanol are introduced into a suitable reaction vessel fitted with a stirrer and a gas inlet. The stirrer is started, the suspension is cooled to 0° C. and 55 g of methylamine are introduced under the level of, that is to say below the surface of, the solvent. After the addition of 10 ml of methanesulfonic acid (catalyst), the reaction mass is heated up and stirred for 3 hours at 50° C. and for 1 hour at 70° C. The suspension is cooled to 10° C. and filtered and the filter cake is washed with cold ethanol. The product is dried in vacuo at elevated temperatures.

Yield: 213 g of sertraline-imine in crude dry form having the following composition:

96.9% 3,4-dichlorosertraline-imine 0.6% 2,3-dichlorosertraline-imine 1.8% sertralone.

The 3,4-dichloro isomer has been enriched from 95% to more than 99%. The yield is 88%. Water and catalyst constitute <0.1%.

EXAMPLE 3

Preparation of Sertraline-imine Isomeric Mixture With Isomer Enrichment in Acetonitrile The procedure is as described in Example 2, except that 650 ml of acetonitrile are used as solvent instead of 800 ml of ethanol.

Yield: 213 g of sertraline-imine in crude dry form having the following composition:

96.8% 3,4-dichlorosertraline-imine 0.7% 2,3-dichlorosertraline-imine 2.3% sertralone.

The 3,4-dichloro isomer has been enriched from 95% to more than 99%. The yield is 88%.

EXAMPLE 4

Recrystallisation and Isomer Enrichment Under Reflux in Ethanol 15.4 g of sertraline-imine isomeric mixture (from Example 2) and 270 ml of ethanol are introduced into a suitable reaction vessel fitted with a stirrer, a nitrogen inlet and a reflux condenser. The reaction mass is put under inert gas, the stirrer is started and the reaction mixture is heated at reflux temperature until a clear solution is obtained. The solution is cooled to 5° C., the product slowly precipitating. The suspension is filtered and the filter cake is washed with cold ethanol and dried.

Yield: 12.9 g (84%) of sertraline-imine having the following composition:
99.3% 3,4-dichlorosertraline-imine
<0.1% 2,3-dichlorosertraline-imine
0.6% sertralone.

EXAMPLE 5

Recrystallisation and Isomer Enrichment Under Pressure in Ethanol 15.4 g of sertraline-imine isomeric mixture (from Example 2) and 120 ml of ethanol are introduced into a suitable pressurized reaction vessel fitted with a stirrer. The reactor is filled with inert gas and sealed, and the stirrer is started. The reaction mixture is heated at 110° C. until a clear solution is obtained. The solution is cooled to 25° C., the product slowly precipitating. The suspension is filtered and the filter cake is washed with cold ethanol and dried.

Yield: 13.2 g (86%) of sertraline-imine having the following composition:
99.2% 3,4-dichlorosertraline-imine
<0.1% 2,3-dichlorosertraline-imine
0.7% sertralone.

EXAMPLES 6 to 13

Recrystallisation and Isomer Enrichment

The following further results are obtained analogously to Examples 4 and 5 (Tab. 1):

EXAMPLE 14

Preparation of Sertraline-imine Isomeric Mixture in Methylamine at 60° C. With Catalyst Sertralone isomeric mixture (95% 3,4-dichlorosertralone, 5% 2,3-dichlorosertralone) and 0.5 g of para-toluenesulfonic acid are introduced into a suitable pressurized reaction vessel (autoclave) fitted with a stirrer and a gas inlet. 24 g of methylamine are then introduced under pressure. The stirrer is started. The reaction mass is heated up and maintained at 60° C. for 5 hours (pressure from 5 to 10 bar), and subsequently cooled to room temperature. The methylamine is released in a controlled manner and the solid product that remains is dried in vacuo.

Yield: 6.9 g of sertraline-imine (corresponding to 100% of theory)

Content: 84.5% 3,4-dichlorosertraline-imine,
4.5% 2,3-dichlorosertraline-imine,
1% sertraline ketone,
3% water,
7% para-toluenesulfonic acid derivatives.

EXAMPLE 15

Preparation of Sertraline-imine Isomeric Mixture in Amines at 50° C. With Acid Catalysis 10 g of sertralone isomeric mixture and 23 g of triethylamine are introduced into a suitable reaction vessel fitted with a stirrer and a gas inlet. The stirrer is started, the suspension is cooled to 0° C. and 3 g of methylamine are

TABLE 1

| Example | Method | Process parameters | Yield | Product composition |
|---|---|---|---|---|
| starting material | without recryst. | sertraline-imine isomeric mixture (see Example 2) | starting material | 3,4-dichloro isomer: 96.4%<br>2,3-dichloro isomer: 0.8%<br>sertralone: 2.7% |
| 6 | $A_1$ | 2.0 g of sertraline-imine, crude form<br>25 ml of 2-propanol<br>isolation at RT | 1.56 g (78%) | 3,4-dichloro isomer: 99.2%<br>2,3-dichloro isomer: <0.1%<br>sertralone: 0.7% |
| 7 | $A_1$ | 10 g of sertraline-imine, crude form<br>30 ml of butyl acetate<br>isolation at RT | 8.4 g (86%) | 3,4-dichloro isomer: 99.3%<br>2,3-dichloro isomer: <0.1%<br>sertralone: 0.6% |
| 8 | $A_1$ | 2.0 g of sertraline-imine, crude form<br>8 ml of isobutyl ethyl ketone<br>isolation at RT | 1.68 g (84%) | 3,4-dichloro isomer: 99.2%<br>2,3-dichloro isomer: <0.1%<br>sertralone: 0.7% |
| 9 | $A_1$ | 3 g of sertraline-imine, crude form<br>9 ml of ethyl methyl ketone<br>isolation at RT | 2.36 g (79%) | 3,4-dichloro isomer: 99.5%<br>2,3-dichloro isomer: <0.1%<br>sertralone: 0.4% |
| 10 | $A_1$ | 3 g of sertraline-imine, crude form<br>15 ml of ethyl acetate<br>isolation at RT | 2.57 g (86%) | 3,4-dichloro isomer: 99.1%<br>2,3-dichloro isomer: <0.1%<br>sertralone: 0.7% |
| 11 | $A_2$ | 3 g of sertraline-imine, crude form<br>6 ml of ethyl acetate<br>temp. 110° C./isolation at RT | 2.53 g (84%) | 3,4-dichloro isomer: 98.9%<br>2,3-dichloro isomer: <0.1%<br>sertralone: 0.8% |
| 12 | $A_1$ | 15.4 g of sertraline-imine, crude form<br>250 ml of acetonitrile<br>isolation at 5° C. | 12.9 g (84%) | 3,4-dichloro isomer: 99.3%<br>2,3-dichloro isomer: <0.1%<br>sertralone: 0.6% |
| 13 | $A_1$ | 3 g of sertraline-imine, crude form<br>10 ml of triethylamine<br>isolation at RT | 2.56 g (85%) | 3,4-dichloro isomer: 99.2%<br>2,3-dichloro isomer: <0.1%<br>sertralone: 0.6% | introduced under the level of, that is to say below the surface of, the solvent. After the addition of 0.65 g (0.1 eq.) of para-toluenesulfonic acid (catalyst), the reaction mass is heated up, stirred for 4 hours at 50° C., and then cooled to 10° C. The suspension is filtered, washed with cold triethylamine and dried in vacuo.

Yield: 8.6 g of sertraline-imine (corresponding to 83% of theory)

94.1% 3,4-dichlorosertraline-imine 0.8% 2,3-dichlorosertraline-imine 4.8% sertralone.

The 3,4-dichloro isomer has been enriched from 95% to more than 99%. The yield is 82%. Water and catalyst constitute <0.2%.

EXAMPLE 16

Preparation of Sertraline-imine at 90° C. Without Acid Catalysis 10 g of sertralone isomeric mixture and 23 g of triethylamine are introduced into a suitable reaction vessel fitted with a stirrer and a gas inlet. The stirrer is started, the suspension is cooled to 0° C. and 3 g of methylamine are introduced under the surface. The reaction mass is heated up, stirred for 10 hours at 90° C. and then cooled to 10° C. The suspension is filtered, washed with cold triethylamine and dried in vacuo.

Yield: 9.0 g of sertraline-imine (corresponding to 87% of theory)

94.3% 3,4-dichlorosertraline-imine 0.7% 2,3-dichlorosertraline-imine 4.8% sertralone.

The 3,4-dichloro isomer has been enriched from 95% to more than 99%. The yield is 87%. The water content is <0.2%.

What is claimed is:

1. A process for the preparation of a compound of formula

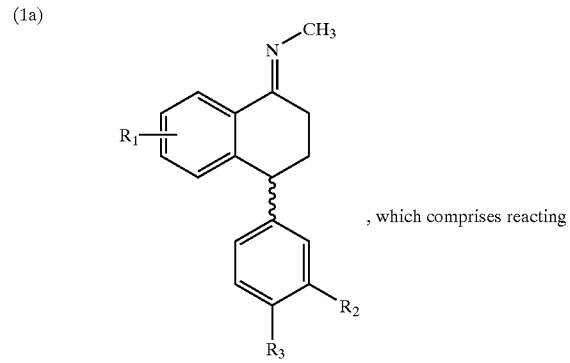

(a) an isomeric mixture consisting of from 75 to 95% of a compound of formula

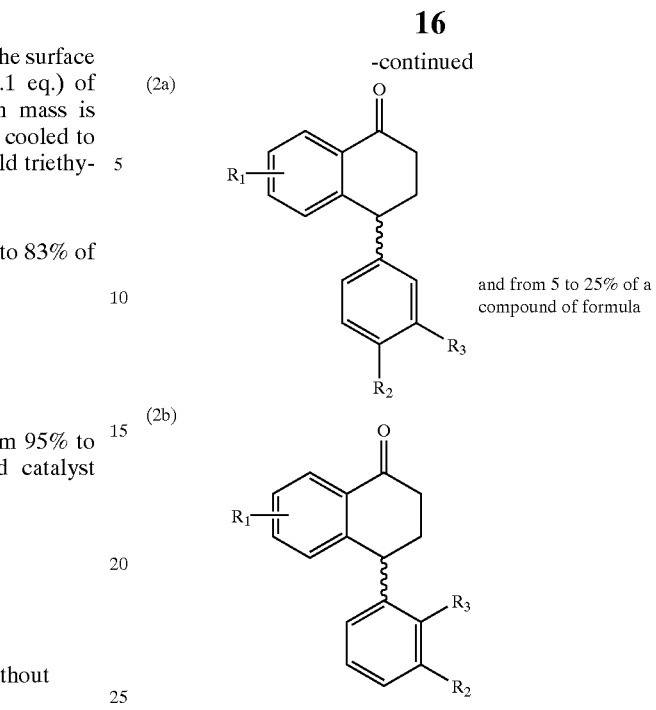

and from 5 to 25% of a compound of formula with methylamine, in a suitable solvent, to form a sertraline-imine isomeric mixture consisting of from 75 to 95% of formula (1a) and from 5 to 25% of formula

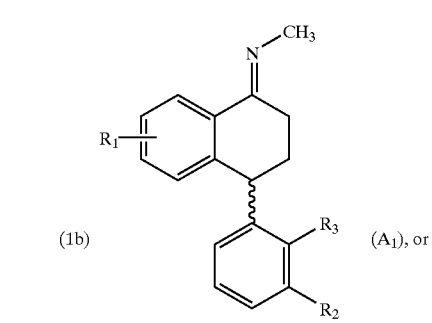

reacting an isomeric mixture consisting of from 75 to 95% of a compound of formula (2a) and from 5 to 25% of a compound of formula (2b) with methylamine, in a suitable solvent, using suitable methods of isolation to form an enriched sertraline-imine isomeric mixture, consisting of >99% of a compound of formula (1a) and <1% of a compound of formula (1b) (A$_2$);

and then subjecting the sertraline-imine isomeric mixture obtained according to reaction route (A$_1$) or (A$_2$), in a suitable solvent, to recrystallisation (B), in accordance with the following scheme:

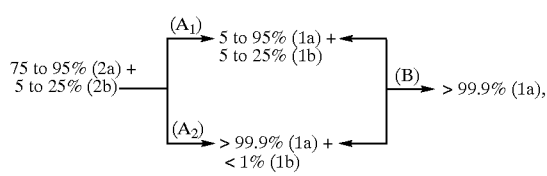

wherein in formulae (1a), (1b), (2a) and (2b)

R$_1$, R$_2$ and R$_3$ are each independently of the others hydrogen, halogen, trifluoromethyl or C$_1$–C$_4$alkoxy.

2. A process according to claim 1, wherein the solvents used for reaction routes (A$_1$) and (A$_2$) are selected from (a) $C_1$–$C_{24}$ amines,
(b) $C_1$–$C_{12}$ nitriles,
(c) $C_2$–$C_{24}$ carboxylic acid esters,
(d) $C_3$–$C_{24}$ ortho esters,
(e) $C_2$–$C_{24}$ ethers,
(f) $C_1$–$C_{24}$ alkanes,
(g) aromatic solvents,
(h) amides,
(i) sulfoxides,
(k) halogenated solvents,
(l) supercritical $CO_2$, and
(m) protic solvents.

3. A process according to claim 1, wherein the solvent (a) is selected from methylamine, nitrogen heterocycles and aliphatic and aromatic, non-substituted or substituted, secondary and tertiary mono-, di- and tri-amines.

4. A process according to claim 3, wherein there is used as solvent (a) a compound of formula

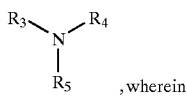
(3)
, wherein $R_3$ is hydrogen; $C_1$–$C_5$ alkyl; hydroxy-$C_1$–$C_5$ alkyl; $C_5$–$C_7$ cycloalkyl; non-substituted phenyl or phenyl substituted by one or more $C_1$–$C_5$ alkyl groups, by halogen or by nitro; non-substituted phenyl-$C_1$–$C_3$ alkyl or phenyl-$C_1$–$C_3$ alkyl substituted by one or more $C_1$–$C_5$ alkyl groups, by halogen or by nitro;

$R_4$ and $R_5$ are each independently of the other $C_1$–$C_5$ alkyl; $C_5$–$C_7$ cycloalkyl; hydroxy-$C_1$–$C_5$-alkyl; non-substituted phenyl or phenyl substituted by one or more $C_1$–$C_5$ alkyl groups, by halogen or by nitro; non-substituted phenyl-$C_1$–$C_3$ alkyl or phenyl-$C_1$–$C_3$ alkyl substituted by one or more $C_1$–$C_5$ alkyl groups, by halogen or by nitro; or $R_4$ and $R_5$ together with the nitrogen atom form a 3- to 6membered heterocyclic radical.

5. A process according to claim 3, wherein there is used as solvent (a) a compound of formula

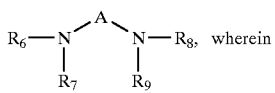
(4)

$R_6$ and $R_8$ are each independently of the other hydrogen; $C_1$–$C_5$ alkyl; or $C_5$–$C_7$ cycloalkyl, $R_7$ and $R_9$ are each independently of the other $C_1$–$C_5$ alkyl; $C_5$–$C_7$ cycloalkyl; non-substituted phenyl or phenyl substituted by one or more $C_1$–$C_5$ alkyl groups, by halogen or by nitro; non-substituted phenyl-$C_1$–$C_3$ alkyl or phenyl-$C_1$–$C_3$ alkyl substituted by one or more $C_1$–$C_5$ alkyl groups, by halogen or by nitro, or $R_6$ and $R_7$, $R_8$ and $R_9$, or $R_7$ and $R_9$, as the case may be, form a 3- to 6-membered heterocyclic radical; and $A_2$ is $C_1$–$C_5$ alkylene.

6. A process according to claim 1, wherein there is used as solvent (b) a compound of formula

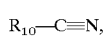
(5) wherein $R_{10}$ is straight-chain or branched $C_1$–$C_{12}$ alkyl; $C_5$–$C_7$ cycloalkyl; non-substituted phenyl or phenyl substituted by one or more $C_1$–$C_5$ alkyl groups, by halogen or by nitro; non-substituted phenyl-$C_1$–$C_3$ alkyl or phenyl-$C_1$–$C_3$ alkyl substituted by one or more $C_1$–$C_5$ alkyl groups, by halogen or by nitro.

7. A process according to claim 1, wherein there is used as solvent (c) a compound of formula

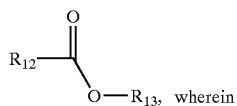
(6)

$R_{12}$ and $R_{13}$ are each independently of the other straight-chain or branched $C_1$–$C_{12}$ alkyl; $C_5$–$C_7$ cycloalkyl; non-substituted phenyl or phenyl substituted by one or more $C_1$–$C_5$ alkyl groups, by halogen or by nitro; non-substituted phenyl-$C_1$–$C_3$ alkyl or phenyl-$C_1$–$C_3$ alkyl substituted by one or more $C_1$–$C_5$ alkyl groups, by halogen or by nitro.

8. A process according to claim 1, wherein there is used as solvent (d) a compound of formula

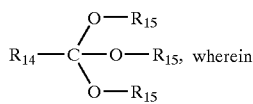
(7)

$R_{14}$ is hydrogen; straight-chain or branched $C_1$–$C_5$ alkyl; or $C_5$–$C_7$ cycloalkyl; and $R_{15}$ is $C_1$–$C_5$ alkyl.

9. A process according to claim 1, wherein there is used as solvent (e) a compound of formula

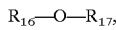
(8) wherein $R_{16}$ and $R_{17}$ are each independently of the other straight-chain or branched $C_1$–$C_{12}$ alkyl; or $C_5$–$C_7$ cycloalkyl; or $R_{16}$ and $R_{17}$ together with the oxygen atom form a 5- to 6-membered radical.

10. A process according to claim 1, wherein there is used as solvent (f) a saturated $C_1$–$C_{22}$ hydrocarbon.

11. A process according to claim 1, wherein the solvent (g) is selected from the group consisting of benzene, toluene, xylene and xylene isomeric mixtures.

12. A process according to claim 1, wherein the solvent (h) corresponds to formula

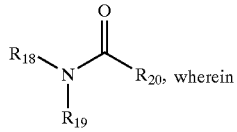
(9)

$R_{18}$ and $R_{19}$ are each independently of the other hydrogen; $C_1$–$C_5$ alkyl; or $C_5$–$C_7$ cycloalkyl, and $R_{20}$ is $C_1$–$C_5$ alkyl; $C_5$–$C_7$ cycloalkyl; non-substituted phenyl or phenyl substituted by one or more $C_1$–$C_5$ alkyl groups, by halogen or by nitro; or non-substituted phenyl-$C_1$–$C_3$ alkyl or phenyl-$C_1$–$C_3$ alkyl substituted by one or more $C_1$–$C_5$ alkyl groups, by halogen or by nitro.

13. A process according to claim 1, wherein the protic solvent (m) is an alcohol.

14. A process according to claim 13, wherein the protic solvent (m) is selected from methanol, ethanol, isopropanol, n-butanol, ethylene glycol, methyl Cellosolve, ethyl Cellosolve, cyclohexanol, glycerol, diethylene glycol, triethanolamine, polyethylene glycol, sec-butanol, n-propanol and tert-butanol.

15. A process according to claim 1, wherein the solvent for purification step (B) is selected from
   (a) $C_1$–$C_{24}$amines,
   (b) $C_1$–$C_{12}$nitriles,
   (c) $C_2$–$C_{24}$carboxylic acid esters,
   (d) $C_3$–$C_{24}$ortho esters,
   (e) $C_2$–$C_{24}$ethers,
   (f) $C_1$–$C_{24}$alkanes,
   (g) aromatic solvents, see above,
   (h) amides,
   (i) sulfoxides, see above,
   (k) halogenated solvents,
   (l) supercritical $CO_2$,
   (m) protic solvents and
   (n) $C_2$–$C_{24}$ketones.

16. A process according to claim 15, wherein the solvent (n) is selected from compounds of formula

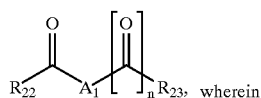

(11)

wherein $R_{22}$ and $R_{23}$ are each independently of the other branched or unbranched $C_1$–$C_{12}$alkyl; $C_5$–$C_7$cycloalkyl; $C_2$–$C_{12}$alkenyl; $C_3$–$C_{12}$alkynyl; non-substituted phenyl or phenyl-$C_1$–$C_3$alkyl, or phenyl or phenyl-$C_1$–$C_3$alkyl substituted by one or more $C_1$–$C_5$alkyl groups;

$A_1$ is a direct bond; or $C_1$–$C_5$alkylene; and n is 0; or 1.

17. A process according claim 1, wherein the solvents are used in the form of individual compounds or in the form of mixtures of two or more individual compounds from the same or different solvent groups (a)–(n).

18. A process according to claim 1, wherein the compound of formula (1a) or (1b) is continuously crystallised out of the reaction medium to a varying extent during the preparation process and subsequently filtered off.

19. A process according claim 18, wherein the filtrate is used in a further reaction for the preparation of a compound of formula (1).

20. A process according to claim 1, wherein the molar ratio of the amount of the compound of formula (2a and 2b) to the amount of methylamine is from 1:1 to 1:1000.

21. A process according to claim 1, wherein reactions ($A_1$) and ($A_2$) are carried out at a temperature of from 20 to 150° C.

22. A process according to claim 1, wherein the reaction is carried out at elevated pressure.

23. A process according to claim 1, wherein, for isolation of a non-enriched sertraline-imine isomeric mixture (reaction route $A_1$), when the reaction is complete the solvent is distilled off, or methylamine or other gaseous amines are released, and the residue obtained is dried.

24. A process according to claim 1, wherein, for isolation of an enriched sertraline-imine isomeric mixture ($A_2$), the reaction mass is cooled, the suspension is filtered, and the filter cake is washed with the solvent.

25. A process according to claim 1, which comprises carrying out reaction ($A_1$) or ($A_2$) in the presence of a catalyst.

26. A process according to claim 25, wherein the catalyst is a protonic acid, a Lewis acid, an aluminium silicate, an ion exchange resin, a zeolite, a naturally occurring layer silicate or a modified layer silicate.

27. A process according to claim 25, wherein the catalyst is a protonic acid.

28. A process according to claim 27, wherein the catalyst is a sulfonic acid.

29. A process according to claim 28, wherein the catalyst is p-toluenesulfonic acid, methanesulfonic acid or camphor-10-sulfonic acid.

30. A process according to claim 1, which comprises carrying out the recrystallisation from the same solvent as reaction ($A_1$) or ($A_2$).

31. A process according to claim 30, which comprises carrying out the recrystallisation under reflux.

32. A process according to claim 30, which comprises carrying out the recrystallisation under elevated pressure.

33. A process according to claim 30, which comprises carrying out the recrystallisation at a temperature of from 50 to 150° C.

34. A process according to claim 30, wherein a cooling gradient in the range from 0.005 to 10° C./min. is employed.

35. A process according to claim 30, wherein the isolation temperature is in the range from −20 to 40° C.

36. A process for the preparation of optically pure (cis)- and/or (trans)-sertraline or an enantiomerically enriched mixture of (cis)- and (trans)-sertraline, which comprises the following reaction steps (I)–(III):

(I) reaction of an isomeric mixture, consisting of from 75 to 95% of formula (2a) and from 25 to 5% respectively of formula (2b), to form the sertraline-imine of formula (1a), corresponding to the process according to claim 1, (II) subsequent cis-selective hydrogenation using a noble metal catalyst or other catalyst based on copper or nickel, to form a cis-sertraline-enriched mixture of racemic cis- and trans-sertraline, and (III) subsequent racemate cleavage based on mandelic acid for the selective preparation of the desired enantiomerically pure cis-isomer.

* * * * *